United States Patent [19]

Maulding

[11] 4,395,577

[45] Jul. 26, 1983

[54] PREPARATION OF 3-CHLOROMETHYL-4-ALKYL-NITROBENZENE BY CHLOROMETHYLATION

[75] Inventor: Donald R. Maulding, Somerville, N.J.

[73] Assignee: American Cyanamid Company, Stamford, Conn.

[21] Appl. No.: 313,855

[22] Filed: Oct. 22, 1981

[51] Int. Cl.$^3$ .............................................. C07C 79/12
[52] U.S. Cl. ..................... 568/936; 71/121; 71/125
[58] Field of Search .................. 71/121, 125; 568/927, 568/936

[56] References Cited

U.S. PATENT DOCUMENTS 4,297,519 10/1981 Ertel ................................... 568/936

Primary Examiner—Leland A. Sebastian
Attorney, Agent, or Firm—Thomas J. Monahan

[57] ABSTRACT

A method for the preparation of 3-chloromethyl derivatives of 4-alkylnitrobenzenes from the corresponding amidomethyl derivatives with phosphorus oxychloride or with phosphorous oxychloride and inert solvents. This process also relates to 3-chloromethyl-4-alkylnitrobenzenes which are useful intermediates for the preparation of certain substituted 2,6-dinitroaniline pre-emergence herbicides.

3 Claims, No Drawings

PREPARATION OF 3-CHLOROMETHYL-4-ALKYL-NITROBENZENE BY CHLOROMETHYLATION

The invention herein described relates to a method for preparation of certain 3-chloromethyl derivatives of 4-alkylnitrobenzenes. These compounds are prepared by reacting appropriate amidomethyl derivatives with either phosphorous oxychloride alone or phosphorus oxychloride and inert solvents. The method of the invention allows the preparation of 3-chloromethyl-4-alkylnitrobenzenes which are useful intermediate compounds involved in the synthesis of certain substituted 2,6-dinitroaniline pre-emergence herbicides.

By way of background, standard methods of chloromethylation involve the use of bis-chloromethyl ether. This compound has unstable, toxic, and corrosive properties and is a known carcinogen. The chloromethylation procedure described in this invention avoids the use of this compound. An object of this invention is to provide a new and useful method for preparing certain chloromethyl derivatives of alkylnitrobenzenes. A further object of this invention is to provide a chloromethylation method which avoids the use of the toxic and unstable bis-chloromethyl ether, and is particularly useful for the preparation of 3-chloromethyl-4-alkylnitrobenzenes which are essential intermediates in the synthesis of certain substituted nitroaniline pre-emergence herbicides. These and further objects are manifest in the following description and particularly delineated in the appended claims.

A method has been discovered for the preparation of compounds of the following structural formula:

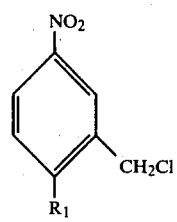

(I)

wherein $R_1$ is $C_1$–$C_4$ alkyl and preferably methyl. These compounds are valuable intermediates in the preparation of certain 2,6-dinitroaniline pre-emergence herbicides of the following structural formula:

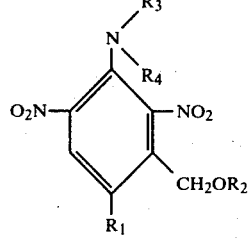

(II)

wherein $R_1$ is $C_1$–$C_4$ alkyl, and preferably methyl; $R_2$ is $C_1$–$C_4$ alkyl; $R_3$ is hydrogen, $C_1$–$C_6$ alkyl, $C_2$–$C_6$ alkenyl or $C_2$–$C_6$ alkynyl; $R_4$ is $C_2$–$C_7$ alkyl (straight or branched), $C_2$–$C_6$ alkenyl, $C_2$–$C_6$ alkynyl, or mono-substituted $C_1$–$C_4$ alkyl where the substituent is halogen or $C_1$–$C_2$ alkoxy.

A formula-I compound may conveniently be prepared by the route illustrated in the following two equations:

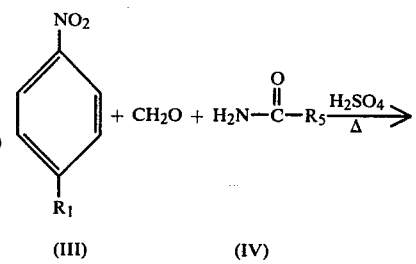

wherein $R_1$ is $C_1$–$C_4$ alkyl, preferably methyl; and $R_5$ is $C_1$–$C_4$ alkyl, preferably methyl, $C_2$–$C_4$ alkenyl, or phenyl.

The sequence yielding formula-I compounds as outlined in the above equations is further characterized as consisting of the following two steps:

(1) A formula-III alkylnitrobenzene is reacted with about 1 to 3 molar equivalents of a formula-IV amide (preferably 3 molar equivalents) and with about 1 to 3 molar equivalents of formaldehyde (preferably 3 molar equivalents) in the presence of a strong acid (i.e., sulfuric acid) at a temperature from about 20° to 60° C. (preferably 50° to 55° C.) for about 10 to 24 hours or until the reaction is essentially complete, thus yielding the appropriate formula-V amidomethyl derivative.

(2) The formula-V amidomethyl compound is then reacted with phosphorus oxychloride or phosphorous oxychloride with a suitable solvent (i.e., methylene chloride, chloroform, ethylene dichloride, benzene, toluene, xylene, chlorobenzene, dimethylformamide, etc., and mixtures thereof) at elevated temperatures (i.e., up to and including the boilding point of the appropriate solvent or solvent mixture) and atmospheric pressure for a period of time sufficient to essentially complete the reaction thus yielding a formula-I compound. The amide to phosphorus oxychloride molar ratio is from 1:1 to 1:4 with the stipulation that when one of the components of the solvent mixture is DMF, then phosphorus oxychloride is present in amounts from one to three molar equivalents per mole of formula-V amide. It is preferable to use 1.5 to 2 moles of phosphorus oxychloride per mole of a formula-V amide in the presence of a solvent mixture consisting of 1.5 to 2 moles of DMF per mole of formula-V amide and another solvent selected from the group named above, especially xylene.

Formula-V compounds can be obtained by an alternative method. A formula IV amide is reacted with formaldehyde by method(s) known in the art to yield the corresponding formula-VI N-hydroxymethylamide having the following structural formula:

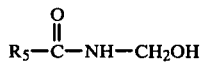

wherein $R_5$ is $C_1-C_4$ alkyl (preferably methyl), $C_2-C_4$ alkenyl, or phenyl. This compound is then reacted with a formula-III 4-alkylnitrobenzene under conditions described above to obtain the appropriate formula-V amidomethyl compound. The following equation illustrates this reaction sequence:

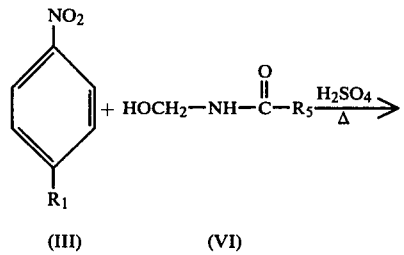

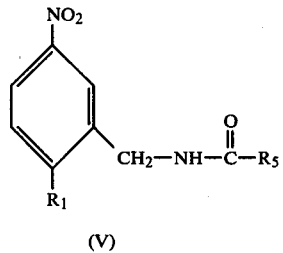

In the above-described processes diacylamides of the following structural formula:

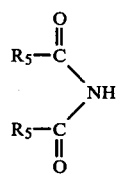

and especially diacetamide may be satisfactorily substituted for the amides of formula-IV where $R_5$ is as defined above.

The formula-I chloromethyl compounds of the invention are valuable intermediates in the preparation of 2,6-dinitroaniline herbicides (i.e., formula-II compounds). These formula-II herbicidal compounds are prepared by reacting an alkali metal alkoxide of formula $MOR_2$ with a $C_1-C_4$ alcohol at reflux temperature for a period of time necessary to complete the reaction and obtain the corresponding formula-VII compound. M is either sodium or potassium and $R_2$ is $C_1-C_4$ alkyl. This reaction is illustrated by the following equation:

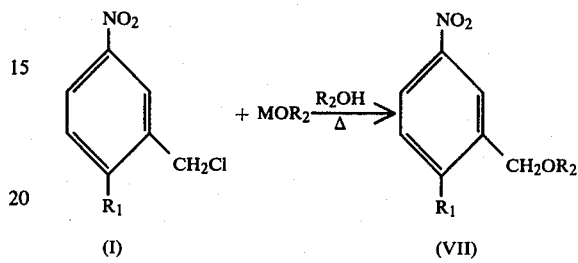

wherein M and $R_2$ are as defined above. The nitro group of the formula-VII ether is then reduced by methods known in the art to yield the corresponding formula-VIII amino compounds as illustrated in the following equation:

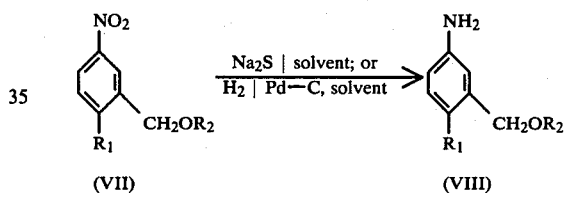

Following this reduction step, the formula-VIII amine is first alkylated and then nitrated to yield the corresponding formula-II dinitroaniline herbicide. This reaction sequence is illustrated by the following equation:

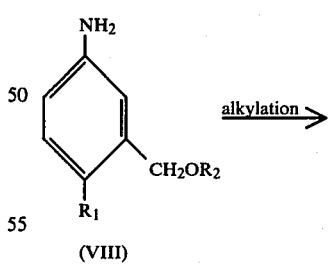

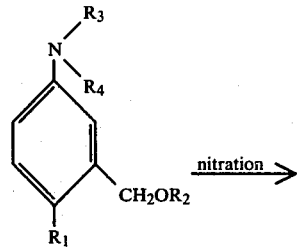

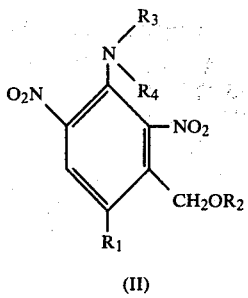

wherein $R_1$ is $C_1$–$C_4$ alkyl; $R_2$ is $C_1$–$C_4$ alkyl; $R_3$ is hydrogen, $C_1$–$C_6$ alkyl, $C_2$–$C_6$ alkenyl, $C_2$–$C_6$ alkynyl, or mono-substituted alkyl $C_1$–$C_4$ where the substituent is halogen or $C_1$–$C_2$ alkoxy. A formula-II pre-emergence herbicide of particular interest which can be prepared by the above methods is N-(1-ethylpropyl)-$\alpha^3$-methoxy-2,6-dinitro-3,4-xylidine.

The formula-II herbicides are usually formulated as solid or liquid compositions comprising an effective amount of the herbicidal agent and a suitable adjuvant. Use of the compositions generally involves application of a herbicidally effective amount of the compounds themselves, or preferably compositions thereof, to the soil containing seeds of undesirable plants.

Formula-II herbicides are typically formulated as dusts, dust concentrates, wettable powders, granulars, and other similar compositions, which are applied by conventional methods at concentrations from about 0.07 to 22 Kg per hectare (preferably 0.28 to 9 Kg per hectare) of active material.

Dusts of formula-II compounds are generally prepared by grinding together on a weight basis about 1 to 15% of the active compound with from about 99 to 85% of a solid diluent (i.e., attaclay, kaolin, diatomaceous earth, fullers earth, talc, pumice, etc.). Dust concentrates are similarly prepared with the exception that about 15 to 95% by weight of active material is used.

Granular formulations of formula-II herbicides are generally prepared by applying a liquid solution of the active compound to appropriate sorptive granular carriers (i.e., attaclay, kaolin, or diatomite granules). Alternatively, formula-II compounds may be mixed with inert carriers and applied to non-sorptive granules (i.e., sand or limestone).

Wettable powders of formula-II herbicides are typically prepared by grinding the active compound with a solid carrier similar to those used in dust formulations. On a weight basis usually about 25 to 75% of the active material and about 73 to 23% of solid carrier are used. Usually about 1 to 5% w/w of a dispersing agent (i.e., alkali metal salts of naphthalene sulfuric acid and anionic-non-ionic blends) and from about 1 to 5% w/w of a surfactant (i.e., polyoxyethylene alcohols, acids, adducts, sorbitan fatty acid esters and sorbitol esters) is added to these compositions. Wettable powder formulations are usually dispersed in water and applied as a liquid spray to the site where control of undesirable plants is desired.

When used as pre-emergence herbicides, dusts or liquid-spray compositions of formula-II compounds are applied to the soil shortly after planting or incorporated into the soil by the pre-plant incorporation technique.

The following non-limiting examples further serve to illustrate the invention.

EXAMPLE 1

Preparation of N-(2-methyl-5-nitrobenzyl)acetamide

To a solution of p-nitrotoluene (0.85 g; 0.05 mol) and para-formaldehyde (1.6 g; 0.05 mol) in concentrated sulfuric acid is added acetamide (8.85 g; 0.15 mol) in increments. This solution is stirred at room temperature for 18 hours. The reaction mixture is then poured onto ice. A precipitate is obtainined which is removed by filtration. This solid material is then mixed with butyl acetate, heated, and filtered while hot to remove insolubles. After cooling, 7.8 g (i.e., 75% yield) of product crystallizes out of solution. The product has the following characteristics: melting point of 141° to 143° C.; i.r. 3275, 1640 and 1660 cm$^{-1}$(sh); mass. spec. m/e 208.

Analysis calculated for $C_{10}H_{12}N_2O_3$: C, 57.69; H, 5.77; N, 13.46; found: C, 57.29; H, 5.77; N, 13.50.

EXAMPLE 2

Preparation of N-(2-methyl-5-nitrobenzyl)acetamide

To a solution of p-nitrotoluene (2.74 g; 0.02 mol) and diacetamide (4.24 g; 0.04 mol) in concentrated sulfuric acid (20 ml) is added aqueous formaldehyde (37%; 1.6 g; 0.02 mol) dropwise with stirring. The reaction mixture is stirred at room temperature for 17 hours, heated to 55° C. for 8 hours and then to 85° C. for 19 hours. The mixture is then poured onto ice. The resulting colorless precipitate is removed by filtration and recrystallized from aqueous ethanol to give 2.7 g of product (65% yield) having a melting point of 133° to 137.5° C.

EXAMPLE 3

Preparation of N-(2-methyl-5-nitrobenzyl)acetamide

A solution of p-nitrotoluene (6.85 g; 0.05 mol) in concentrated sulfuric acid (60 ml) is cooled in an ice bath and N-(hydroxymethyl)acetamide (4.45 g; 0.05 mol) is added. The reaction mixture is stirred until a solution is obtained and then continuously stirred for 16 hours at 55° C. The mixture is then poured onto ice and the resulting precipitate is isolated. This solid material is extracted with 85 ml of butyl acetate on a steambath. Concentration of the butyl acetate solution with subsequent cooling gives 3.9 g (i.e., 38% yield) of product. The butyl acetate insoluble material (2.5 g) is methylene bis(4-nitro-o-toluene).

EXAMPLE 4

Preparation of N-(2-ethyl-5-nitrobenzyl)acetamide

4-Ethylnitrobenzene (7.55 g; 0.05 mol) is added in small increments to a stirred solution of acetamide (5.9 g; 0.05 mol) and paraformaldehyde (1.6 g; 0.05 mol) in concentrated sulfuric acid (60 ml). This reaction mixture is stirred for 17 hours at 55° C. and then poured onto ice. A precipitate results which is recrystallized from butyl acetate to give 6.2 g (i.e., 56% yield) of product. This product has the following characteristics: melting point of 123° to 128° C.; i.r. 3275, 1640 and 1660 cm$^{-1}$ (sh); mass. spec. m/e 222.

Analysis calculated for $C_{11}H_{14}N_2O_3$: C, 59.46; H, 6.31; N, 12.61; found: C, 59.30; H, 6.45; N, 12.03.

EXAMPLE 5

Preparation of N-(2-methyl-5-nitrobenzyl)acrylamide

Acrylamide (7.10 g; 0.10 mol) is added in small increments to a stirred solution of p-nitrotoluene (1.85 g; 0.05 mol) and paraformaldehyde (1.6 g; 0.05 mol) in concentrated sulfuric acid (60 ml). This reaction mixture is stirred for 24 hours at room temperature and then poured onto ice. A precipitate results which is collected and recrystallized from ethyl acetate to give 4.4 g of product as colorless crystals. This product has the following characteristics: melting point of 155° to 158.5° C.; i.r. 3230, 1620, 1655, 1660 cm$^{-1}$(sh).

Analysis calculated for $C_{11}H_{12}N_2O_5$: C, 10.00; H, 5.45; N, 12.73; found: C, 59.72; H, 5.48; N, 12.50.

EXAMPLE 6

Preparation of N-(hydroxymethyl)acetamide

The compound N-(hydroxymethyl)acetamide is prepared from acetamide and paraformaldehyde using the procedure described by Walter et al., Chem. Ber., 99: 3204 (1966).

EXAMPLE 9

Preparation of 2-Methyl-5-nitrobenzyl chloride

A solution of N-(2-methyl-5-nitrobenzyl)acetamide (3.12 g; 0.015 mol), phosphorus oxychloride (5.12 g; 0.032 mol) and dimethylformamide (2.19 g; 0.03 mol) in xylene (50 ml) is refluxed for one hour. The reaction mixture is then washed with water and the solvent evaporated. This treatment produces 2.36 g (i.e., 85% yield) of product having a melting point of 56° to 62° C.

Additional experiments using the above-described procedure are performed with variations of reactants, reactant ratios, solvents (and mixtures thereof), reaction time and temperatures. Results of these experiments are presented in Table I.

TABLE I

Various Preparations of 2-methyl-5-nitrobenzyl chloride from N—(2-methyl-5-nitrobenzyl) acetamide (i.e., amide) by the method of Example 9

| | Moles of Reactants used | | | | Reaction | | | Product | | Molar ratios of reactants amide:POCl$_3$(SOCl$_2$): |
|---|---|---|---|---|---|---|---|---|---|---|
| Example | "amide" | POCL$_3$ | SOCL$_2$ | DMF | Solvent/ml | time/h | Temperature | Yield % | m.p. °C. | DMF |
| 9 | 0.015 | 0.032 | | 0.03 | xylene/50 | 1 | reflux | 85 | 56–62 | 1:2.1:2.0 |
| 10 | 0.01 | 0.04 | | | POCl$_3$/3.65 | 3 | reflux | 50 | 50–57 | 1:4.0 |
| 11 | 0.015 | 0.032 | | | MCB/50 | 1.5 | reflux | 67 | 55–62 | 1:2.1:0 |
| 12 | 0.015 | 0.022 | | 0.19 | DMF/15 | 3 | 125° C. | 58 | oil | 1:1.47:12.9 |
| 13 | 0.015 | 0.016 | | 0.02 | Toluene/50 | 16 | reflux | 40 | 57–62 | 1:1.07:1.33 |
| 14 | 0.015 | 0.016 | | | EDC/25 | 6 | reflux | 50 | 57–60 | 1:1.07:0 |
| 15 | 0.015 | 0.016 | | | MCB/50 | 5 | reflux | 30 | 56.5–59.5 | 1:1.07:0 |
| 16 | 0.015 | 0.016 | | | EDC/50 | 16 | reflux | 55 | oil | 1:1.07:0 |
| 17 | 0.015 | | 0.032 | | MCB/50 | 4 | 125° C. | | | 1:2.1:0 |
| 18 | 0.01 | | 0.04 | | SOCl$_2$/2.9 | 1.25 | reflux | | | 1:4.0:0 |
| 19 | 0.015 | | 0.016 | 0.19 | DMF/15 | 2 | 100° C. | 24 | n.a. | 1:1.07:12.9 |
| 20 | 0.015 | | 0.022 | 0.19 | DMF/15 | 3 | 125° C. | | | 1:1.47:12.9 |
| 21 | *0.01 | | 0.03 | | EDC/30 | 4 | reflux | | | 1:3:0 |
| 22 | 0.015 | | 0.016 | | EDC/25 | 5 | reflux | | | 1:1.07:0 |
| 23 | 0.015 | [PCl$_5$; 0.015] | | | MCB/50 | 1.5 | reflux | | | 1:1:0 |

Legend:
*N—(2-methyl-5-nitrobenzyl)benzamide is used in this experiment.
DMF = dimethylformamide
EDC = ethylene dichloride
MCB = chlorobenzene
n.a. = not available

EXAMPLE 7

Preparation of N-(hydroxymethyl)benzamide

The compound N-(hydroxymethyl)benzamide is prepared in 84% yield from benzamide and formaldehyde using the procedure described by Monti, Gazz. Chim., 50: 39 (1930).

EXAMPLE 8

Preparation of N-(2-methyl-5-nitrobenzyl)benzamide

N-hydroxymethyl benzamide (7.55 g; 0.05 mol) is added to a solution of p-nitrotoluene (0.85 g; 0.05 mol) in concentrated sulfuric acid (60 ml). The reaction mixture is stirred for 63 hours at room temperature and then poured onto ice. A colorless precipitate is obtained which is isolated and recrystallized repeatedly from aqueous ethanol to give 4.0 g (i.e., 30% yield) of product. Increasing the reaction time to 7 days gives a 43% yield of product compound. This product has the following characteristics: melting point of 134° to 137° C.; i.r. 3300, 1635, 1655 cm$^{-1}$ (sh); mass. spec. m/e 270.

Analysis calculated for $C_{15}H_{14}N_2O_3$: C, 11.67; H, 5.78; N, 10.37; found: C, 66.54; H, 5.10; N, 10.12.

EXAMPLE 24

Preparation of Methyl 2-methyl-5-nitrobenzyl ether

2-Methyl-5-nitrobenzyl chloride (10.2 g) is dissolved in methanol (180 ml). Sodium methoxide (5.4 g) is added and the mixture is refluxed. The reaction is monitored by thin layer chromatography (75:25, hexane:benzene). Additional quantities of sodium methoxide are added and heating continues until the reaction is complete. The reaction mixture is then cooled and filtered. The filtrate is concentrated under vacuum. The residue is dissolved in methylene chloride, washed with water, and the organic layer is then dried over magnesium sulfate. Removal of the drying agent by filtration and concentration of the filtrate under vacuum leaves 15.8 g of solid material which when recrystallized from hexane (150 ml) yields 11.5 g of product as a white solid having a melting point from 45° to 52° C.

Analysis calculated for $C_9H_{11}NO_5$: C, 59.66; H, 6.12; N, 7.73; found: C, 59.65; H, 6.17; N, 7.64.

EXAMPLE 25

Preparation of 3-(Methoxymethyl)-p-toluidine

Methyl 2-methyl-5-nitrobenzyl ether (11.5 g) is dissolved in absolute ethanol (125 ml). A solution of sodium sulfide monohydrate (48.3 g) and sodium bicarbonate (16.7 g) in water (75 ml) is added to the alcoholic solution. The resulting mixture is refluxed until thin layer chromatography indicates that the starting material is exhausted. The reaction mixture is then concentrated under vacuum to an oily solid. Methylene chloride is added and the mixture filtered. The methylene chloride layer is separated, dried, and is concentrated under vacuum to yield 9.3 g of a mobile orange liquid.

EXAMPLE 26

Preparation of N-(1-ethylpropyl)-3-(methoxymethyl)-p-toluidine

A mixture of 3-(methoxymethyl)-p-toluidine (9.3 g), 5 angstrom molecular sieves (19 g) and diethyl ketone (40 ml) is stirred at room temperature for 15 hours. The mixture is then filtered. Additional diethyl ketone (10-15 ml) and molecular sieves (10 g) are added to the filtrate. After 40 minutes at 40° to 50° C., the reaction mixture is filtered and then concentrated under vacuum. The crude product (9.0 g) is dissolved in methanol (50 ml) and cooled to 10° C. Sodium borohydrate (3.7 g) and methanol (25 ml) are simultaneously added in small portions. Thirty minutes after these additions, the mixture is acidified with 10% hydrochloric acid while in an ice bath. The mixture is extracted with ether and the ether extract is discarded. The aqueous extract is made alkaline and then extracted with ether. The ether extract is dried over magnesium sulfate and concentrated to yield 8.1 g of an orange oil which is more than 97% homogeneous as estimated by gas-liquid chromatography. Fractional distillation yields a product having a boiling point of 120° to 125° C. at 0.4 to 0.5 mm pressure.

Analysis calculated for $C_{14}H_{23}ON$: C, 75.97; H, 10.47; N, 0.33; found: C, 75.87; H, 10.62; N, 6.24.

EXAMPLE 27

Preparation of N-(1-ethylpropyl)-$\alpha^3$-methoxy-2,6-dinitro-3,4-xylidine

A solution of N-(1-ethylpropyl)-3-(methoxymethyl)-p-toluidine in dichloroethane (10 ml) is added to a nitrating mixture consisting of 3.78 g of nitric acid, 3.0 g of concentrated sulfuric acid and 1.4 g of water at 30±3° C. Following this addition the reaction mixture is held at 30±3° C. for 3 hours. It is then poured into water and extracted with methylene chloride. The methylene chloride layer is dried over magnesium chloride and concentrated under vacuum to yield a residue of 3.2 g. The residue is purified on a silica gel column with benzene as the eluant. All fractions shown by thin-layer chromatography to contain the same compound are combined to yield 1.3 g of an orange solid having a melting point of 55° to 57° C. A sample is recrystallized for analysis from hexane and has a melting point of 56° to 57° C.

Analysis calculated for $C_{14}H_{21}O_5N_3$: C, 54.01; H, 6.80; N, 13.50; found: C, 54.00; H, 6.69; N, 13.44.

EXAMPLE 28

Evaluation of the pre-emergence herbicidal activity of N-(1-ethylpropyl)-3-(methoxymethyl)-2,6-dinitro-p-toluidine The pre-emergence herbicidal activity of N-(1-ethylpropyl)-3-(methoxymethyl)-2,6-dinitro-p-toluidine is demonstrated by several tests in which seeds of a variety of monocotyledonous and dicotyledonous plants are individually mixed with potting soil and planted on top of approximately 2.5 cm soil in separate 375 ml (pint) cups. After planting, the cups are sprayed with the selected aqueous acetone solution containing N-(1-ethylpropyl)-3-(methoxymethyl)-2,6-dinitro-p-toluidine at a concentration equivalent to 0.03 to 1.2 kg per hectare of test compound. The treated cups are then placed on greenhouse benches, watered and cared for in accordance with conventional greenhouse procedures. Three or four weeks after treatment the tests are terminated and each cup is examined and rated according to the rating system set forth in Table II.

TABLE II

Rating System Utilized in Pre-emergence Herbicide Experiments

| Scale | % Difference in Growth from Control* |
|---|---|
| 0 = no effect | 0 |
| 1 = possible effect | 1-10 |
| 2 = slight effect | 11-25 |
| 3 = moderate effect | 26-40 |
| 5 = definite injury | 41-60 |
| 6 = herbicidal effect | 61-75 |
| 7 = good herbicidal effect | 76-90 |
| 8 = approaching complete kill | 91-99 |
| 9 = complete kill | 100 |
| 4 = abnormal growth, i.e., a definite physiological malformation but with an over-all effect less than a 5 on the rating scale. | |

*Based on visual determination of stand, size, vigor, chlorosis, growth malformation and overall plant appearance.

Plant abbreviations utilized in pre-emergence herbicide experiments are presented in Table III.

TABLE III

| Plant Abbreviations | | |
|---|---|---|
| Code | Common Name | Scientific Name |
| SE | Sesbania | Sesbania exaltata |
| MU | Mustard | Brassica kaber |
| PI | Pigweed | Amaranthus Retroflexus |
| RW | Ragweed | Ambrosia artemisiifolia |
| MG | Morningglory | Ipomoea purpurea |
| TW | Teaweed | Sida spinosa |
| VL | Velvetleaf | Abutilon theophrasti |
| BA | Barnyardgrass | Echinochloa crusgalli |
| CR | Crabgrass | Digitaria sanguinalis |
| GF | Green Foxtail | Setaria viridis |
| WO | Wild Oats | Avena fatua |
| CN | Corn | Zea mays |
| CO | Cotton | Gossypium hirsutum |
| SY | Soybean | Glycine max |

The results of pre-emergence herbicidal activity experiments with the compound N-(1-ethylpropyl)-3-(methoxymethyl)-2,6-dinitro-p-toluidine are presented in Table IV. These data show that this compound is an effective pre-emergence herbicide against various monocotyledonous and dicotyledonous plants.

TABLE IV

Herbicidal evaluation of N—(1-ethylpropyl)-3-(methoxymethyl)-2,6-dinitro-p-toluidine.

| COMPOUND | RATE kg/ha | SE | MU | PI | RW | MG | TW | VL | BA | CR | GF | WO | CN | CO | SY |
|---|---|---|---|---|---|---|---|---|---|---|---|---|---|---|---|
| 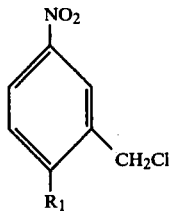 | 1.12 | 7.6 | 7.5 | 8.7 | 3.6 | 4.3 | 8.5 | 8.3 | 9 | 9 | 9 | 2.4 | 3.0 | .6 | .9 |
| | 0.56 | 5.3 | 8.5 | 8.5 | 3.6 | 2.5 | 8.3 | 7.5 | 9 | 9 | 9 | 0.9 | 1.3 | 0 | 0 |
| | 0.28 | 2.4 | 7.6 | 8.1 | 0 | 0.7 | 7.6 | 5.9 | 8.8 | 9 | 9 | 0.7 | 0 | 0 | 0 |
| | 0.14 | 1.0 | 5.4 | 5.8 | 0 | 0 | 6.8 | 3.2 | 8.7 | 8.9 | 9 | 0 | 0 | 0 | 0 |
| | 0.07 | 0 | 2.1 | 3.8 | 0 | 0 | 3.9 | 1.1 | 6.5 | 8.9 | 8.5 | 0 | 0 | 0 | 0 |
| | 0.035 | 0 | 0 | 1.1 | 0 | 0 | 0.8 | 0 | 4.6 | 8.2 | 6.1 | 0 | 0 | 0 | 0 |

*The data are averages of two or more tests.

What is claimed is:

1. A process for the preparation of a compound of structural formula:

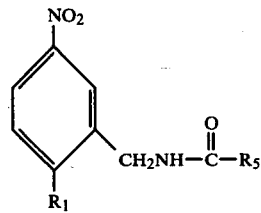

wherein $R_1$ is $C_1$–$C_4$ alkyl, comprising reacting an amide of structural formula:

wherein $R_1$ is $C_1$–$C_4$ alkyl, $R_5$ is $C_1$–$C_4$ alkyl, $C_2$–$C_4$ alkenyl, or phenyl, with phosphorus oxychloride alone or with phosphorus oxychloride in the presence of a solvent methylene chloride, chloroform, ethylene dichloride, benzene, toluene, xylene, chlorobenzene, dimethylformamide or mixtures thereof, at elevated temperatures up to and including the boiling point of the solvent or solvent misture, for a period of time sufficient to essentially complete the reaction, and wherein the amide to phosphorus oxychloride molar ratio is in the range of from 1:1 to 1:4; with the condition that when one of the components of the solvent mixture is dimethylformamide, then it is present in the solvent mixture in amounts of one to three molar equivalents per mole of amide.

2. A process according to claim 1, wherein $R_1$ is alkyl $C_1$–$C_4$; $R_5$ is methyl; the solvent is selected from ethylene dichloride, toluene, xylene, chlorobenzene, dimethylformamide and mixtures thereof; the amide to phosphorus oxychloride ratio is in the range of 1:1.5 to 1:2.1, and when the solvent mixture contains dimethylformamide, it is present in the mixture in 1.5 to 2 molar equivalents per mole of amide.

3. A process according to claim 2, wherein $R_1$ and $R_5$ are both methyl; the reaction is carried out in the presence of a dimethylformamide-xylene solvent mixture, and the amide to phosphorus oxychloride to dimethylformamide molar ratio is 1:2.1:2.

* * * * *